United States Patent [19]

Walsh

[11] Patent Number: 5,063,235

[45] Date of Patent: Nov. 5, 1991

[54] 4-[(DIARYL)HYDROXYMETHYL]-1-PIPERIDINEALKANOLS AND ESTERS AND CARBAMATES THEREOF USEFUL IN THE TREATMENT OF ALLERGIC DISORDERS

[75] Inventor: David A. Walsh, Richmond, Va.

[73] Assignee: A. H. Robins Company, Inc., Richmond, Va.

[21] Appl. No.: 516,570

[22] Filed: Apr. 30, 1990

[51] Int. Cl.$^5$ .................... A61K 31/445; C07D 211/22
[52] U.S. Cl. ...................... 514/317; 514/318; 514/331; 546/239; 546/193; 546/234; 546/194; 546/236
[58] Field of Search ............ 546/238, 239, 193; 514/317, 318

[56] References Cited

U.S. PATENT DOCUMENTS

| | | | |
|---|---|---|---|
| 3,687,956 | 8/1972 | Zirkovic | 546/230 |
| 3,941,795 | 3/1976 | Carr | 546/240 |
| 4,812,451 | 3/1989 | Shanklin | 546/193 |
| 4,950,674 | 8/1990 | Yanni et al. | 514/318 |

*Primary Examiner*—Jane T. Fan
*Assistant Examiner*—Celia Chang
*Attorney, Agent, or Firm*—Richard K. Jackson

[57] ABSTRACT

Novel compounds of the formula:

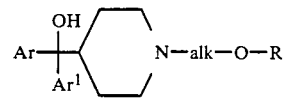

are disclosed wherein Ar and Ar$^1$ are phenyl, sustituted phenyl or pyridinyl, "alk" is a $C_1$-$C_{12}$ straight or branched hydrocarbon chain, and R is H, loweralkylcarbonyl, arylcarbonyl, or aminocarbonyl where the amino is unsubstituted or substituted by one or two groups selected from loweralkyl or aryl. The compounds of this invention are useful in the treatment of allergic disorders.

6 Claims, No Drawings

4-[(DIARYL)HYDROXYMETHYL]-1-PIPERIDINEALKANOLS AND ESTERS AND CARBAMATES THEREOF USEFUL IN THE TREATMENT OF ALLERGIC DISORDERS

BACKGROUND OF THE INVENTION

1. Field of Invention

This invention relates to novel 4-[(diaryl)hydroxymethyl]-1-piperidinealkanols and their esters and carbamates which are useful in treating allergic disorders. The compounds are useful in combatting allergic responses in a living animal body in need thereof and pharmaceutical compositions therefor. More specifically the methods employ the compounds inhibiting Type I allergic responses (Gell and Coombs Classification of Immune Responses) by antagonizing end organ effects of mediators involved in the immediate hypersensitivity response and as such are useful in treating allergic phenomena which includes asthma, rhinitis, atopic dermatitis, chronic hives, allergic conjunctivitis and the like.

2. Information Disclosure Statement

4-[Bis(aryl)hydroxymethyl]piperidines used in the synthesis of compounds of this invention are disclosed in U.S. Pat. Nos. 3,956,296; 4,032,642; 4,810,713 and 4,886,794. The 4-diarylmethyl (or methylene) piperidine and 1-diarylmethylpiperazine moieties are not uncommon in pharmaceutical research, especially in the area of drugs affecting the central nervous system. These moieties are also useful in other areas of pharmaceutical research. For example, our U.S. Pat. No. 4,810,713 discloses a method of treating allergy with aryl ether compounds having the formula:

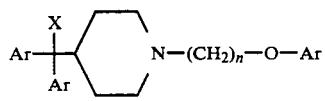

where X is H, OH, CN or forms a double bond with the piperidine ring carbon at the 4-position. The European Patent Application EP 94,159 discloses some dihydropyridinecarboxylate esters of 1-benzhydryl-4-piperazineethanol as having antihypertensive effects of long duration.

SUMMARY OF THE INVENTION

The novel compounds of this invention are the 4-(diaryl)hydroxymethyl-1-piperidinealkanols, the esters, and carbamates thereof corresponding to Formula I:

Formula I

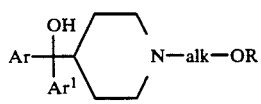

wherein Ar and $Ar^1$ can be independently phenyl, 2,3 or 4-pyridinyl or

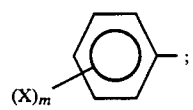

"alk" is a straight or branched hydrocarbon chain containing 2-12 carbons; R is H,

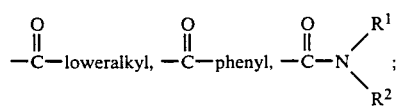

X is selected from halogen, trifluoromethyl, loweralkyl, loweralkoxy, or hydroxy; m is 0-3; $R^1$ and $R^2$ are independently selected from H, loweralkyl, phenyl or

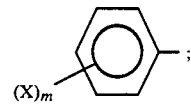

when m is more than 1 the values of X may be the same or different; the optical isomers thereof and the pharmaceutically acceptable addition salts. In the further definition of symbols in the formula hereof and where they appear elsewhere throughout this specification and claims, the terms have the following significance:

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like. "Loweralkoxy" has the formula "—O—loweralkyl."

The terms 'halogen or halo' include chlorine, bromine, fluorine and iodine radicals. The "alk" straight or branched hydrocarbon chain containing 2-12 carbons is exemplified by ethylene (—(CH$_2$)$_2$—), propylene (—(CH$_2$)$_3$—), isopropylene

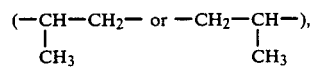

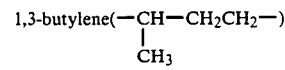

pentyl, hexyl, octyl and the like.

Pharmaceutically acceptable addition salts includes those salts formed by the free bases of compounds of Formula I and pharmaceutically acceptable acids such as the hydrochloride, hydrobromide, sulfate, phosphate, fumarate, succinate, oxalate, hexamate and the like and hydrates or solvates thereof.

The primary screening method used to detect antiallergy properties of compounds of Formula I is a modification of the procedure of R. R. Martel and J. Klicius, INTERN. ARCH. ALLERGY APPL. IMMUNOLOGY. 54, pp. 205-209 (1977) which measures the effect of oral administration of the compound on the volume of a rat paw which was previously injected with an anti-egg albumin serum and is described under Pharmacology Method hereinbelow. The Gell and Combs Classification of Immune Responses referred to is well known in the art and is described in ESSENTIAL IMMUNOLOGY, 3rd edition (1977, Blackwell Scientific Publications). It is therefore a primary object of the present invention to provide novel 4-[(diaryl)hydroxymethyl]piperidine-alkanols and esters and carbamates thereof useful in treating allergic disorders in living animals. Another object is to provide a method of treatment and still another object to provide pharmaceutical compositions therefor.

Additional objects and advantages of the present invention will be apparent to one skilled in the art and others will become apparent from the following description of the best mode of carrying out the present invention and in the appended claims.

DETAILED DESCRIPTION OF THE INVENTION

Compounds of Formula I are prepared by the methods illustrated in the following schematic equations.

The reaction mixture is then concentrated under reduced pressure and the residue partitioned between water and a suitable water-immiscible solvent such as methylene chloride or benzene. The organic layer containing the product free base is separated, dried and concentrated and the product purified as the free base form or converted to a pharmaceutically acceptable acid addition salt.

Equation B illustrates the methods of transforming the Formula I alcohols into the esters and carbamates. These reactions are performed under water-excluding conditions using a solvent such as methylene chloride or benzene which is non-reactive with the acylating

A.

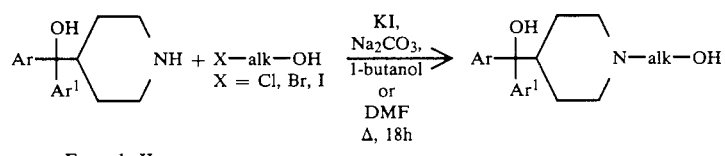

Formula II

B.

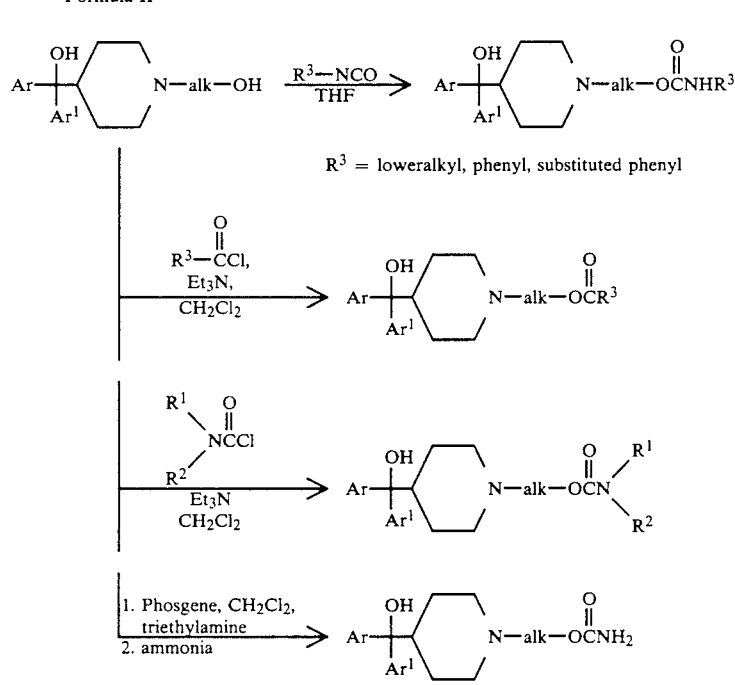

C.

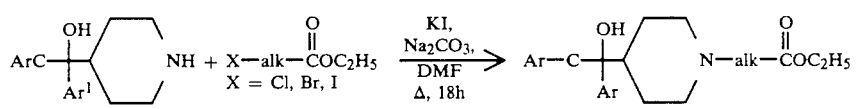

Formula II

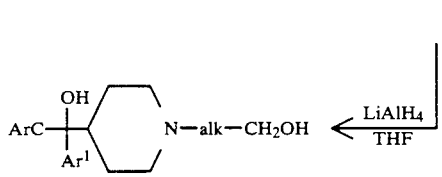

In equation A the 4-[(diaryl)hydroxymethyl]-1-piperidinealkanols are formed from a 4-[(diaryl)hydroxymethyl]piperidine of Formula II and a haloalkanol under conventional nucleophilic displacement conditions, usually by heating the reactants for several hours in n-butanol or N,N-dimethylformamide (DMF) with an inorganic base such as sodium carbonate or sodium bicarbonate and a catalytic amount of potassium iodide.

agents, i.e., an isocyanate, acid chloride, or carbamyl chloride. Reactions using isocyanates and acid chlorides are usually conducted at room temperature. Reactions using carbamyl chlorides are usually conducted at the boiling temperature of the solvent used. The reaction mixture is filtered to remove triethylamine hydrochloride if present. Unreacted acid chlorides or carbamyl chlorides can be removed by extraction with a dilute base, such as dilute sodium hydroxide or aqueous sodium carbonate or sodium bicarbonate. The organic layer is separate, dried, and concentrated to obtain the product free base which is purified using conventional laboratory procedures such as crystallization or chromatography and transformed into a pharmaceutically acceptable salt and the salt purified by conventional laboratory techniques.

Equation C represents an alternate method of preparing the 4-[(diaryl)hydroxymethyl]-1-piperidinealkanols where the Formula II intermediate is alkylated with an haloalkylcarboxylic acid ester as in Equation A and the carboxy group is reduced with a reducing agent known to reduce a carboxylic acid ester to the alcohol such as lithium aluminum hydride. This process will extend the chain length of the "alk" group by one methylene unit.

The 4-[(diaryl)hydroxymethyl]piperidines are prepared as described in U.S. Pat. Nos. 3,956,296; 4,032,642; 4,810,713 and 4,886,794 and also in J. Med. Chem., 1989, 32, 105. The chemical reactions described above are generally disclosed in terms of their broadest application to the preparation of compounds of this invention and shold not be construed as limiting in any way. Occasionally the reactions may not be applicable as described to each compound within the disclosed scope, but this should be readily apparent to those skilled in the art. In all such cases, the reactions can be successfully performed by conventional modifications known to those skilled in the art or by changing to alternative reagents, by routine modification of reaction conditions, etc. In all preparative methods, all starting materials are known or readily preparable form known starting materials.

Without further elaboration, it is believed that one skilled in the art can, using the preceeding description, utilize the present invention to its fullest extent. The following specific examples are, therefore, to be construed as merely illustrative, and not limitative of the remainder of the disclosure in any way whatsoever.

PREPARATION 1

4-[Bis(4-fluorophenyl)hydroxymethyl]-1-piperidineacetic acid ethyl ester (E)-2-butenedioate (1:1)

A mixture of 4.6 g (0.015 mol) of 4-[bis(4-fluorophenyl)hydroxymethyl]piperidine, 2.5 g (0.015 mol) of ethyl bromoacetate, 6.4 g (0.061 mol) of anhydrous sodium carbonate and 0.3 g (0.002 mol) of potassium iodide in 50 mL of N,N-dimethylformamide was heated on a steam bath for 16 h. The mixture was poured into 1 L of water and extracted thrice with 250 mL portions of ethyl acetate. The combined organic extracts were washed with water and brine, dried (MgSO$_4$) and concentrated under reduced pressure to give 6.0 g of a dark oil. The oil was purified by high pressure liquid chromatography (Waters Associates Prep LC/System 500A); PrepPAK 500 silica; ethyl acetate-hexane 1:2 l flow rate 200 mL/min). The fractions containing the desired product were combined and concentrated under reduced pressure to give a colorless oil. The oil was converted to the fumaric acid salt and the solid was recrystallized from 2-propanol to yield 4.7 g (62%) of the title compound as a white solid, mp 178°–180° C.

Analysis: Calc. for $C_{22}H_{25}F_2NO_3.C_4H_4O_4$: C, 61.78; H, 5.78; N, 2.77; Found: C, 61.87; H, 5.76; N, 2.82.

PREPARATION 2

4-[Bis(4-fluorophenyl)hydroxymethyl]-1-piperidinebutanoic acid ethyl ester ethanedioate (1:1)

A mixture of 4.6 g (0.015 mol) of 4-[bis(4-fluorophenyl)hydroxymethyl]piperidine, 2.9 g (0.015 mol) of ethyl 4-bromobutyrate, 6.4 g (0.061 mol) of anhydrous sodium carbonate and 0.3 g (0.002 mol) of potassium iodide in 50 mL of N,N-dimethylformamide gave 7.2 g of a dark oil. The oil was converted to the oxalic acid salt and the solid was recrystallized from 2-propanol to yield 6.2 g (82%) of the title compound as a white solid, mp 164°–166° C.

Analysis: Calc. for $C_{24}H_{29}F_2NO_3.C_2H_2O_4$: C, 61.53; H, 6.16; N, 2.76; Found: C, 61.32; H, 6.53; N, 2.62.

PREPARATION 3

4-[Bis(4-fluorophenyl)hydroxymethyl]-1-piperidinepentanoic acid ethyl ester ethanedioate (1:1)

This compound was prepared according to the procedure of Preparation 1. A mixture of 4.6 g (0.015 mol) of 4-[bis(4-fluorophenyl)hydroxymethyl]piperidine, 3.2 g (0.015 mol) of ethyl 5-bromovalerate, 6.4 g (0.061 mol) of anhydrous sodium carbonate and 0.3 g (0.002 mol) of potassium iodide in 50 mL of N,N-dimethylformamide gave 6.8 g of a dark oil. The oil was converted to the oxalic acid salt and the solid was recrystallized from 2-propanol to yield 5.7 g (73%) of the title compound as a white solid, mp 162°–163° C.

Analysis: Calc. for $C_{25}H_{31}F_2NO_3.C_2H_2O_4$: C, 62.18; H, 6.38; N, 2.69; Found: C, 62.12; H, 6.41; N, 2.75.

EXAMPLE 1

4-[bis(4-fluorophenyl)hydroxymethyl]-1-piperidinepropanol

A mixture of 30.3 g (0.10 mole) of $\alpha,\alpha$-bis(4-fluorophenyl)-4-piperidinemethanol, 16.1 g (0.11 mole) of 3-bromo-1-propanol (95% purity, Aldrich), 37.1 g (0.35 mole) of anhydrous sodium carbonate and 1.0 g of potassium iodide in 300 ml of DMF was heated on a steam bath for 20 h. The mixture was converted and the residue partitioned between water and benzene. The benzene layer was washed with water and brine, dried (sodium sulfate) and concentrated to give a gummy solid. The solid was recrystallized from 2-propanol/isopropyl ether to yield 23.3 g (65%) of a white solid, mp 155°–157° C.

Analysis: Calculated for $C_{21}H_{25}F_2NO_2$: C, 69.79; H, 6.97; N, 3.88; Found: C, 69.80; H, 7.10; N, 3.84.

EXAMPLE 2

4-[Bis(4-fluorophenyl)hydroxymethyl]-1-piperidineethanol ethanedioate (1:1)

A solution of 30.0 g (0.077 mol) of 4-[bis(4-fluorophenyl)hydroxymethyl]-1-piperidine acetic acid ethyl ester in 250 mL of dry (freshly distilled from lithium aluminum hydride) tetrahydrofuran was added dropwise to a stirred solution of 7.3 g (0.192 mol) of lithium aluminum hydride in 200 mL of dry tetrahydrofuran. After the final addition, the mixture was stirred at ambient temperature for 1 h, whereupon the excess lithium aluminum hydride was quenched by successive dropwise additions of 8 mL of water, 8 mL of 15% sodium hydroxide solution, and 24 mL of water. The solution was then filtered, and the filtrate was concentrated under reduced pressure to yield 22.7 g (85%) of a yellow glass. A portion of the glass was converted to the oxalic acid salt, and the salt was recrystallized from 2-propanol to give the title compound as a white solid, mp 170°–172° C.

Analysis: Calculated for $C_{20}H_{23}F_2NO_2 \cdot C_2H_2O_4$: C, 60.41; H, 5.76; N, 3.20; Found: C, 60.08; H, 5.93; N, 3.15.

EXAMPLE 3

4-[Bis(4-fluorophenyl)hydroxymethyl]-1-piperidinebutanol

A solution of 15.4 g (0.037 mol) of 4-[bis(4-fluorophenyl)hydroxymethyl]-1-piperidinebutanoic acid ethyl ester in 100 mL of dry (freshly distilled from lithium aluminum hydride) tetrahydrofuran was added dropwise to a mixture of 3.5 g (0.092 mol) of lithium aluminum hydride in 100 mL of dry tetrahydrofuran. After the final addition, the mixture was stirred at ambient temperature for 3 h, whereupon the excess lithium aluminum hydride was quenched by successive dropwise additions of 4 mL of water, 4 mL of 15% sodium hydroxide solution and 12 mL of water. The mixture was stirred for 30 min, filtered, and the filtrate concentrated under reduced pressure to yield 11.2 g (100%) of an oil which crystallized upon standing. A portion of the solid was recrystallized from ethyl acetate/petroleum ether (30°–60° C.) to give the title compound as a light-tan solid, mp 130°–131° C.

Analysis: Calculated for $C_{22}H_{27}F_2NO_2$: C, 70.38; H, 7.25; N, 3.73; Found: C, 70.36; H, 7.30; N, 3.70.

EXAMPLE 4

4-[Bis(4-fluorophenyl)hydroxymethyl]-1-piperidinehexanol ethanedioate (1:1)

A mixture of 7.0 g (0.023 mole) of α,α-bis(4-fluorophenyl)-4-piperidinemethanol, 3.2 g (0.023 mol) of 6-chloro-1-hexanol, 9.8 g (0.093 mol) of anhydrous sodium carbonate, and 0.4 g (0.002 mol) of potassium iodide in 100 mL of N,N-dimethylformamide was heated on a steam bath for 16 h. The mixture was poured into 1 L of water and extracted thrice with 250 mL portions of ethyl acetate. The ethyl acetate fractions were combined, washed with water and brine, dried (MgSO$_4$), and concentrated under reduced pressure to yield 9.0 g (97%) of a yellow glass. A portion of the glass was converted to the oxalic acid salt, and the solid oxalate was recrystallized from 2-propanol to give a white solid, mp 129°–130° C.

Analysis: Calculated for $C_{24}H_{31}F_2NO_2 \cdot C_2H_2O_4$: C, 63.27; H, 6.74; N, 2.84; Found: C, 62.82; H, 6.89; N, 2.79.

EXAMPLE 5

4-[Bis(4-fluorophenyl)hydroxymethyl]-1-piperidinepentanol hemihydrate

A solution of 16.8 g (0.040 mol) of 4-[bis(4-fluorophenyl)hydroxymethyl]-1-piperidinepentanoic acid ethyl ester in 100 mL of dry (freshly distilled from lithium aluminum hydride) tetrahydrofuran was added dropwise to a solution of 3.8 g (0.100 mol) of lithium aluminum hydride in 100 mL of dry tetrahydrofuran while stirring vigorously at ambient temperature for 1 h and the excess lithium aluminum hydride was quenched by successive, dropwise additions of 4 mL of water, 4 mL of a 15% sodium hydroxide solution, and 12 mL of water. The solution was allowed to stir for 30 min, filtered, and the filtrate concentrated under reduced pressure to yield 11.5 g (98%) of an off-white solid. A portion of the solid was recrystallized from ethyl acetate/petroleum ether (30°–60° C.) to give the title compound as a white solid, mp 103°–105° C.

Analysis: Calculated for $C_{23}H_{29}F_2NO \cdot 0.5H_2O$: C, 69.32; H, 7.59; N, 3.52; Found: C, 69.44; H, 7.56; N, 3.45.

EXAMPLE 6

4-[Bis(4-fluorophenyl)hydroxymethyl]-1-piperidineoctanol

A mixture of 7.0 g (0.023 mol) of α,α-bis(4-fluorophenyl)-4-piperidinemethanol, 5.0 g (0.024 mol) of 8-bromo-1-octanol, 9.8 g (0.093 mol) of anhydrous sodium carbonate and 0.4 g (0.002 mol) of potassium iodide in 100 mL of N,N-dimethylformamide was heated on a steam bath for 3 h. The mixture was poured into 1 L of water and extracted thrice with 250 mL portions of ethyl acetate. The ethyl acetate fractions were combined, washed with water and brine, dried (MgSO$_4$), and concentrated under reduced pressure to give a gold oil which crystallized upon trituration with petroleum ether (30°–60° C.). The solid was recrystallized from ethyl ether/petroleum ether (30°–60° C.) to yield 10.0 g (100%) of white solid, mp 97°–98° C. $^1$H NMR analysis confirmed the presence of 0.25 eq. of water.

Analysis: Calculated for $C_{26}H_{35}F_2NO_2 \cdot 0.25H_2O$: C, 71.61; H, 8.21; N, 3.21; Found: C, 71.80; H, 8.25; N, 3.23.

EXAMPLE 7

4-[Bis(4-fluorophenyl)hydroxymethyl]-1-piperidinepropanol acetate ester ethanedioate (1:1)

A solution of 1.3 g (0.017 mol) of acetyl chloride in 50 mL of tetrahydrofuran was added dropwise to a solution of 5.4 g (0.015 mol) of 4-[bis(4-fluorophenyl)hydroxymethyl]-1-piperidinepropanol and 3.0 g (0.030 mol) of triethylamine in 100 mL of tetrahydrofuran. The mixture was stirred at ambient temperature for 16 h. The mixture was filtered to remove the solid precipitate, and the filtrate was concentrated under reduced pressure to give a yellow oil. The oil was converted to the oxalic acid salt and the solid recrystallized from 2-propanol to yield 7.0 g (95%) of the title compound as a white solid, mp 186°–188° C.

Analysis: Calculated for $C_{23}H_{27}F_2NO_3 \cdot C_2H_2O_4$: C, 60.85; H, 5.92; N, 2.84; Found: C, 60.54; H, 6.08; N, 3.22.

EXAMPLE 8

4-[Bis(4-fluorophenyl)hydroxymethyl]-1-piperidinepropanol benzoate ester

A solution of 1.7 g (0.012 mol) of benzoyl chloride in 25 mL of tetrahydrofuran was added dropwise to a solution of 3.6 g (0.010 mol) of 4-[bis(4-fluorophenyl)hydroxymethyl]-1-piperidinepropanol and 2.0 g (0.020 mol) of triethylamine in 100 mL of tetrahydrofuran. The mixture was stirred at ambient temperature for 4 h, filtered to remove the solid precipitate, and the filtrate concentrated under reduced pressure to give a brown solid. The solid was dissolved in ethyl acetate and filtered through a small bed of silica gel eluting with ethyl acetate. The fractions containing the desired product were combined and concentrated under reduced pressure to give a white solid. The solid was recrystallized from ethyl acetate/isopropyl ether to yield 3.2 g (69%) of white solid, mp 147°–148° C.

Analysis: Calculated for $C_{28}H_{29}F_2NO_3$: C, 72.24; H, 6.28; N, 3.01; Found: C, 72.16; H, 6.28; N, 3.03.

EXAMPLE 9

4-[Bis(4-fluorophenyl)hydroxymethyl]-1-piperidinepropanol dimethylcarbamic acid ester ethanedioate (1:1)

A solution of 5.4 g (0.015 mol) of 4-[bis(4-fluorophenyl)hydroxymethyl]-1-piperidinepropanol, 4.0 g (0.04 mol) of triethylamine and 3.2 g (0.03 mol) of dimethylcarbamoyl chloride in 150 mL of benzene was heated at reflux for 24 h. The solution was cooled, treated with 25 mL of water and vigorously stirred. The mixture was filtered and the filtrate layers were separated. The organic layer was washed with a saturated solution of sodium bicarbonate, dried ($Na_2SO_4$) and concentrated to give 5.2 g of gum as residue. The gum was purified by column chromatography on 100 g of Florisil. Fractions eluted with 5–15% acetone in benzene were combined and concentrated to give a gum as residue. This gum was converted to the oxalic acid salt and the solid was recrystallized from 95% ethanol to yield 2.2 g (28%) of the title compound as a white solid, mp 211°–213° C. (dec.).

Analysis: Calculated for $C_{26}H_{32}F_2N_2O_7$: C, 59.76; H, 6.17; N, 5.36; Found: C, 59.90; H, 6.20; N, 5.36.

EXAMPLE 10

4-[Bis(4-fluorophenyl)hydroxymethyl]-1-piperidinepropanol methylcarbamate ester ethanedioate (1:1)

A solution of 1.2 g (0.020 mol) of methyl isocyanate in 50 mL of methylene chloride was added dropwise to a solution of 5.4 g (0.015-01) of 4-[bis(4-fluorophenyl)hydroxymethyl]-1-piperidinepropanol in 100 mL of methylene chloride. After the final addition, the solution was heated at reflux for 16 h. The solution was washed with water and brine, dried ($MgSO_4$) and concentrated under reduced pressure to give a glass. The glass was converted to the oxalic acid salt, and the solid was recrystallized from 2-propanol to yield 6.6 g (87%) of the title compound as a white solid, mp 135°–137° C.

Analysis: Calculated for $C_{23}H_{28}F_2N_2O_3 \cdot C_2H_2O_4$: C, 59.05; H, 5.95; N, 5.51; Found: C, 58.92; H, 6.00; N, 5.52.

EXAMPLE 11

4[Bis(4-fluorophenyl)hydroxymethyl]-1-piperidinepropanol phenylcarbamate ester ethanedioate (1:1)

A solution of 0.2 g (0.017 mol) of phenyl isocyanate in 50 mL of methylene chloride was added dropwise to a solution of 4.0 g (0.011 mol) of 4-[bis(4-fluorophenyl)hydroxymethyl]-1-piperidinepropanol in 100 mL of methylene chloride. After the final addition, the solution was stirred at ambient temperature for 2 h. The solution was washed with water and brine, dried ($MgSO_4$), concentrated, and the residue was converted to the oxalic acid salt. The salt was recrystallized from 2-propanol to yield 5.4 g (87%) of white solid, mp 161°–163° C.

Analysis: Calculated for $C_{28}H_{30}F_2N_2O_3 \cdot C_2H_2O_4$: C, 63.15; H, 5.65; N, 4.91; Found: C, 63.13; H, 5.71; N, 4.91.

EXAMPLE 12

3-[4-[Bis(4-fluorophenyl)hydroxymethyl]-1-piperidinyl]propanol diphenylcarbamate ester ethanedioate (1:1)

A solution of 2.3 g (0.010 mol) of diphenylcarbamyl chloride in 50 mL of tetrahydrofuran was added dropwise to a solution of 3.0 g (0.008 mol) of 4-[bis(4-fluorophenyl)hydroxymethyl]-1-piperidinepropanol and 2.0 g (0.020 mol) of triethylamine in 100 mL of tetrahydrofuran. The solution was heated to reflux for 72 h before a precipitate started to form. A catalytic amount of N,N-dimethylformamide was added, and reflux was continued for 10 days. The mixture was filtered to remove the solid precipitate, and the filtrate was concentrated under reduced pressure to give a dark oil. The oil was purified by column chromatography using 100 g of silica gel in a 60 cm × 3.5 cm column, eluted with ethyl acetate. The fractions containing the desired product were combined and concentrated under reduced pressure to give a yellow glass. The glass was converted to the oxalic acid salt, and the solid was recrystallized from 2-propanol to yield 2.5 g (48%) of white solid, mp 193°–195° C.

Analysis: Calculated for $C_{34}H_{34}N_2O_3 \cdot C_2H_2O_4$: C, 66.86; H, 5.61; N, 4.33; Found: C, 66.52; H, 5.72; N, 4.24.

EXAMPLE 13

3-[4-[Bis(4-fluorophenyl)hydroxymethyl]-1-piperidinyl]propanol methylphenylcarbamate ester ethanedioate (1:1)

A solution of 2.0 g (0.012 mol) of N-methyl-N-phenylcarbamoyl chloride in 75 mL of tetrahydrofuran was added dropwise to a solution of 3.6 g (0.010 mol) of 4-[bis(4-fluorophenyl)hydroxymethyl]-1-piperidinepropanol and 2.0 g (0.020 mol) of triethylamine in 50 mL of tetrahydrofuran. The mixture was heated at reflux under a nitrogen atmosphere for 7 days. The solution was filtered to remove a precipitate, and the filtrate was concentrated under reduced pressure to give a viscous gum. The gum was purified by column chromatography using 150 g of silica gel on a 60 cm × 3.5 cm column, eluted wit 5% methanol in methyene chloride. The fractions containing the desired product were combined and concentrated under reduced pressure. The residue was converted to the oxalic acid salt, and the salt was recrystallized from 2-propanol to yield 4.0 g (68%) of white solid, mp 200°–201° C.

Analysis: Calculated for $C_{29}H_{32}F_2N_2O_3 \cdot C_2H_2O_4$: C, 63.69; H, 5.86; N, 4.79, Found: C, 63.79; H, 5.97; N, 4.83.

EXAMPLE 14

4-[Bis(4-fluorophenyl)hydroxymethyl]-1-piperidineethanol methycarbamate ester hydrochloride hydrate (2:2:1)

A solution of 0.8 g (0.014 mol) of methyl isocyanate in 50 mL of methylene chloride was added dropwise to a solution of 3.0 g (0.009 mol) of 4-[bis(4-fluorophenyl)hydroxymethyl]-1-piperidineethanol in 50 mL of methylene chloride. The mixture was heated at reflux for 24 h and then stirred at ambient temperature for 36 h. The solution was then concentrated under reduced pressure to give a yellow glass. The glass was converted to the hydrochloric acid salt, and the solid was recrystallized from 2-propanol/ethyl ether to yield 3.2 g (81%) of the title compound as a white solid, mp 225°–226° C.

Analysis: Calc. for $C_{22}H_{26}F_2N_2O_3 \cdot HCl \cdot 0.5H_2O$: C, 58.73; H, 6.27; N, 6.23, Found: C, 59.15; H, 6.34; N, 6.32.

EXAMPLE 15

4-[Bis(4-fluorophenyl)hydroxymethyl]-1-piperidinebutanol methycarbamate ester ethanedioate (1:1)

A solution of 1.0 g (0.018 mol) of methyl isocyanate in 25 mL of methylene chloride was added dropwise to a solution of 4.0 g (0.011 mol) of 4-[bis(4-fluorophenyl)-hydroxymethyl]-1-piperidinebutanol in 50 mL of methylene chloride. The solution was heated at reflux for 16 h, cooled, and concentrated under reduced pressure to give a glass. The glass was converted to the oxalic acid salt and the solid was recrystallized from 2-propanol to yield 3.5 g (61%) of white solid, mp 183°–184° C.

Analysis: Calc. for $C_{24}H_{30}F_2N_2O_3.C_2H_2O_4$: C, 59.76; H, 6.17; N, 5.36; Found: C, 59.65; H, 6.32; N, 5.27.

EXAMPLE 16

4-[Bis(4-fluorophenyl)hydroxymethyl]-1-piperidineoctanol methycarbamate ester

A solution of 2.0 g (0.035 mol) of methyl isocyanate in 25 mL of methylene chloride was added dropwise to a solution of 4.4 g (0.10 mol) of 4-[bis(4-fluorophenyl)-hydroxymethyl]-1-piperidineoctanol in 75 mL of methylene chloride. After the final addition the solution was heated at reflux for 24 h and stirred at ambient temperature for 48 h. The solution was washed with water and brine, dried (MgSO4), and concentrated under reduced pressure to give a yellow solid. The solid was recrystallized from benzene to yield 3.3 g (68%) of white solid, mp 124°–125° C.

Analysis: Calculated for $C_{28}H_{38}F_2N_2O_3$: C, 68.83; H, 7.84; N, 5.73; Found: C, 68.76; H, 7.62; N, 5.68.

EXAMPLE 17

4-[Bis(4-fluorophenyl)hydroxymethyl]-1-piperidinehexanol methylcarbamate ester

A solution of 1.2 g (0.021 mol) of methyl isocyanate in 25 mL of methylene chloride was added dropwise to a solution of 4.5 g (0.011 mol) of 4-[bis(4-fluorophenyl)-hydroxymethyl]-1-piperidinehexanol in 25 mL of methylene chloride. After the final addition the solution was heated at reflux for 24 h. The solution was cooled, washed with water and brine, dried (MgSO4), and concentrated under reduced pressure to give a yellow solid. The solid was recrystallized from benzene/petroleum ether (30°–60° C.) to yield 2.2 g (44%) of white solid, mp 126°–128° C.

Analysis: Calculated for $C_{26}H_{34}F_2N_2O_3$: C, 67.81; H, 7.44; N, 6.08; Found: C, 67.96; H, 7.58; N, 6.21.

EXAMPLE 18

4-[Bis(4-fluorophenyl)hydroxymethyl]-1-piperidineethanol dimethylcarbamate ester ethanedioate (1:1)

A solution of 2.2 g (0.020 mol) of dimethylcarbamyl chloride in 25 mL of tetrahydrofuran was added dropwise to a solution of 3.0 g (0.009 mol) of 4-[bis(4-fluorophenyl)hydroxymethyl]-1-piperidineethanol and 4.5 g (0.045 mol) of triethylamine in 75 mL of tetrahydrofuran. After the final addition, the solution was heated at reflux for 15 days. The mixture was filtered to remove the solid precipitate, and the filtrate was concentrated under reduced pressure. The residue was partitioned between benzene and water and stirred for 30 min. The benzene layer was washed with water and brine, dried (MgSO4), and concentrated under reduced pressure to give a gum. The gum was purified by column chromatography using 50 g of silica gel on a 60 cm×2 cm column, eluted with 10% methanol in methylene chloride. The combined fractions containing the desired product were concentrated under reduced pressure to give a glass. The glass was converted to the oxalic acid salt, and the solid was recrystallized from 2-propanol to yield 1.4 g (31%) of the title compound as a white solid, mp 167°–169° C.

Analysis: Calculated for $C_{23}H_{28}F_2N_2O_3.C_2H_2O_4$: C, 59.05; H, 5.95; N, 5.51; Found: C, 59.23; H, 6.07; N, 5.51.

EXAMPLE 19

4-[Bis(4-fluorophenyl)hydroxymethyl]-1-piperidinepentanol methylcarbamate ester ethanedioate hydrate (2:2:1)

A solution of 1.2 g (0.021 mol) of methyl isocyanate in 50 mL of methylene chloride was added dropwise to a solution of 4.0 g (0.010 mol) of 4-[bis(4-fluorophenyl)-hydroxymethyl]-1-piperidinepentanol in 100 mL of methylene chloride. The mixture was heated at reflux for 24 h and then stirred at ambient temperature for 36 h. The solution was concentrated under reduced pressure to give a yellow oil. The oil was converted to the oxalic acid salt, and the solid was recrystallized from 2-propanol to yield 4.0 g (75%) of the title compound as a white solid, mp 115°–117° C.

Analysis: Calc. for $C_{25}H_{32}F_2N_2O_3.C_2H_2O_4.0.5H_2O$: C, 59.44; H, 6.47; N, 5.13; Found: C, 59.72; N, 6.63; N, 5.11.

EXAMPLE 20

4-[Bis(4-fluorophenyl)hydroxymethyl]-1-piperidinebutanol dimethylcarbamate ester ethanedioate hydrate (2:2:1)

A solution of 3.2 g (0.030 mol) of dimethylcarbamyl chloride in 50 mL of tetrahydrofuran was added dropwise to a solution of 4.0 g (0.011 mol) of 4-[bis(4-fluorophenyl)hydroxymethyl]-1-piperidinebutanol and 6.0 g (0.059 mol) of triethylamine in 150 mL of tetrahydrofuran and the mixture was heated at reflux for 15 days. The mixture was filtered and the filtrate concentrated under reduced pressure. The residue was partitioned between methylene chloride and water. The methylene chloride layer was washed with water and brine, dried (MgSO4) and concentrated under reduced pressure to give a dark oil. The oil was purified by column chromatography using 50 g of silica gel on a 60 cm×2 cm column, eluted with 10% methanol in methylene chloride. Fractions containing the desired product were combined and concentrated under reduced pressure to give a glass. The glass was converted to the oxalic acid salt, and the solid was recrystallized from 2-propanol to yield 2.0 g (34%) of the title compound as a white solid, mp 133°–135° C.

Analysis: Calc. for $C_{25}H_{32}F_2N_2O_3.C_2H_2O_4.0.5H_2O$: C, 59.44; H, 6.47; N, 5.13; Found: C, 59.31; H, 6.31; N, 5.01.

EXAMPLE 21

Following the procedure of Example 1 and substituting the following 4-[(diaryl)hydroxymethyl]piperidines for 4-[bis(4-fluorophenyl)hydroxymethyl]piperidine:
  a. α,α-bis(4-methylphenyl)-4-piperidinemethanol
  b. α,α-bis(4-methoxyphenyl)-4-piperidinemethanol
  c. α,α-bis(4-chlorophenyl)-4-piperidinemethanol
  d. α-(4-fluorophenyl)-α-phenyl-4-piperidinemethanol
  e. α,α-diphenyl-4-piperidinemethanol
  f. α-(4-fluorophenyl)-α-(4-piperidinyl)-2-pyridinemethanol
  g. α-(4-piperidinyl)-α-(2-pyridinyl)-2-pyridinemethanol
there are obtained respectively a. 4-[hydroxybis(4-methylphenyl)methyl]-1-piperidinepropanol
b. 4-[hydroxybis(4-methoxyphenyl)methyl]-1-piperidinepropanol
c. 4-[bis(4-chlorophenyl)hydroxymethyl]-1-piperidinepropanol
d. 4-[(4-fluorophenyl)hydroxyphenylmethyl]-1-piperidinepropanol
e. 4-(hydroxydiphenylmethyl)-1-piperidinepropanol
f. 4-[(4-fluorophenyl)hydroxy(2-pyridinyl)methyl]-1-piperidinepropanol
g. 4-[hydroxybis(2-pyridinyl)methyl]-1-piperidinepropanol

TABLE 1

| Example | Ar | Ar1 | alk | R | Salt |
|---|---|---|---|---|---|
| 1 | 4-F—$C_6H_4$ | 4-F—$C_6H_4$ | —$(CH_2)_3$— | H | — |
| 2 | 4-F—$C_6H_4$ | 4-F—$C_6H_4$ | —$(CH_2)_2$— | H | oxalate |
| 3 | 4-F—$C_6H_4$ | 4-F—$C_6H_4$ | —$(CH_2)_4$— | H | — |
| 4 | 4-F—$C_6H_4$ | 4-F—$C_6H_4$ | —$(CH_2)_6$— | H | oxalate |
| 5 | 4-F—$C_6H_4$ | 4-F—$C_6H_4$ | —$(CH_2)_5$— | H | $0.5H_2O$ |
| 6 | 4-F—$C_6H_4$ | 4-F—$C_6H_4$ | —$(CH_2)_8$— | H | — |
| 7 | 4-F—$C_6H_4$ | 4-F—$C_6H_4$ | —$(CH_2)_3$— | —C(O)—$CH_3$ | oxalate |
| 8 | 4-F—$C_6H_4$ | 4-F—$C_6H_4$ | —$(CH_2)_3$— | —C(O)—$C_6H_5$ | — |
| 9 | 4-F—$C_6H_4$ | 4-F—$C_6H_4$ | —$(CH_2)_3$— | —C(O)—$N(CH_3)_2$ | oxalate |
| 10 | 4-F—$C_6H_4$ | 4-F—$C_6H_4$ | —$(CH_2)_3$— | —C(O)—$NHCH_3$ | oxalate |
| 11 | 4-F—$C_6H_4$ | 4-F—$C_6H_4$ | —$(CH_2)_3$— | —CNH$C_6H_5$ (O) | oxalate |
| 12 | 4-F—$C_6H_4$ | 4-F—$C_6H_4$ | —$(CH_2)_3$— | —CN$(C_6H_5)_2$ (O) | oxalate |
| 13 | 4-F—$C_6H_4$ | 4-F—$C_6H_4$ | —$(CH_2)_3$— | —CN$(CH_3)C_6H_5$ (O) | oxalate |
| 14 | 4-F—$C_6H_4$ | 4-F—$C_6H_4$ | —$(CH_2)_2$— | —CNH$CH_3$ (O) | HCl.$0.5H_2O$ |
| 15 | 4-F—$C_6H_4$ | 4-F—$C_6H_4$ | —$(CH_2)_4$— | —CNH$CH_3$ (O) | oxalate |
| 16 | 4-F—$C_6H_4$ | 4-F—$C_6H_4$ | —$(CH_2)_8$— | —CNH$CH_3$ (O) | — |
| 17 | 4-F—$C_6H_4$ | 4-F—$C_6H_4$ | —$(CH_2)_6$— | —CNH$CH_3$ (O) | — |
| 18 | 4-F—$C_6H_4$ | 4-F—$C_6H_4$ | —$(CH_2)_2$— | —CN$(CH_3)_2$ (O) | oxalate |
| 19 | 4-F—$C_6H_4$ | 4-F—$C_6H_4$ | —$(CH_2)_5$— | —CNH$CH_3$ (O) | oxalate.$0.5H_2O$ |
| 20 | 4-F—$C_6H_4$ | 4-F—$C_6H_4$ | —$(CH_2)_4$— | —CN$(CH_3)_2$ (O) | oxalate.$0.5H_2O$ |
| 21a | 4-$CH_3C_6H_4$— | 4-$CH_3C_6H_4$— | —$(CH_2)_3$— | H | — |
| 21b | 4-$CH_3OC_6H_5$— | 4-$CH_3OC_6H_4$— | —$(CH_2)_3$— | H | — |
| 21c | 4-Cl$C_6H_4$— | 4-Cl$C_6H_4$— | —$(CH_2)_3$— | H | — |
| 21d | 4-F—$C_6H_4$— | $C_6H_5$— | —$(CH_2)_3$— | H | — |
| 21e | $C_6H_5$— | $C_6H_5$— | —$(CH_2)_3$— | H | — |

TABLE 1-continued

| Example | Ar | Ar1 | alk | R | Salt |
|---------|-----|-----|------|---|------|
| 21f | 4-F—$C_6H_5$— | (pyridyl ring) | —$(CH_2)_3$— | H | — |
| 21g | (pyridyl ring) | (pyridyl ring) | —$(CH_2)_3$— | H | — |

Pharmacology Methods Antiallergy Screening Method—Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205–209(1977) in which the effect of oral administration of the compound on the volume of a rat paw which was previously injected with anti-egg albumin serum and followed by egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control aricles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml)±S.D. A significant decrease ($p<0.05$) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used ot determine relative potency.

| Passive Foot Anaphylaxis Assay | |
|---|---|
| Compound of Example | % Reduction with test drug/ % Reduction with reference drug* |
| 1 | −79/−74 |
| 2 | −67/−81 |
| 3 | −74/−81 |
| 4 | −74/−81 |
| 5 | −72/−81 |
| 6 | −72/−68 |
| 7 | −37/−79 |
| 8 | −51/−67 |
| 9 | −80/−57 |
| 10 | −79/−67 |
| 11 | −72/−77 |
| 12 | −14/−67 |
| 13 | −83/−75 |
| 14 | −71/−84 |
| 15 | −67/−84 |
| 16 | −86/−81 |
| 17 | −69/−81 |
| 18 | −87/−68 |
| 19 | −76/−67 |
| 20 | −91/−67 |

*test drug given at 10 mg/kg P.O.
reference drug (aminophylline) given at 100 mg/kg P.O.

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways; for example, orally as in elixirs, capsules, tablets or coated tablets, parenterally in the form of sterile solutions, suspensions, and in some cases intravenously in the form of sterile solutions, intranasally and to the throat or bronchial region in the form of drops, gargles, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the pharmacology tests on rats in comparison to certain other antiallergy drugs suggest an effective dose for an adult will be in the range of 5 to 50 mg for the more active compounds with a daily dosage amounting to about 20 to 200 mg/day.

Based on the animal data, unit dosages containing an amount of compound equivalent to about 0.7 to 0.7 mg of active drug per kilogram of body are contemplated. Daily dosages of about 0.3 to 30 mg/kg of body weight are contemplated for humans and obviously several small dosage forms may be adminstered at one time. However, the amount of the active compounds administered need not be limited by these contemplations due to uncertainty in transposing animal data to human treatment.

Examples of compositions within the preferred ranges given are as follows:

| Capsules | |
|---|---|
| Ingredients | Per Cap. |
| 1. Active ingredient | 10.0 mg |
| 2. Lactose | 146.0 mg |
| 3. Magnesium Stearate | 4.0 mg |

Procedure
1. Blend 1, 2 and 3.
2. Mill this blend and blend again.
3. This milled blend is then filled into #1 hard gelatin capsules.

| Tablets | |
|---|---|
| Ingredients | Per Cap. |
| 1. Active ingredient | 10.0 mg |
| 2. Corn Starch | 20.0 mg |
| 3. Alginic acid | 20.0 mg |
| 4. Sodium alginate | 20.0 mg |
| 5. Magnesium Stearate | 1.3 mg |

Procedure
1. Blend 1, 2, 3 and 4.
2. Add sufficient water portionwise to the blend from Step #1 with careful stiring after each addition. Such additions of water and stirring continue until the mass is of consistency to permit its conversion to wet granules.
3. The wet mass is converted to granules by passing it through the oscillating granulator, using 8 mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg |
| 2. pH 4.0 Buffer solution q.s. to | 1.0 ml |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml. |
| 1. Active ingredient | 5.0 mg |
| 2. Isotonic Buffer solution 4.0 q.s. to | 1.0 ml |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per ml. |
| 1. Active ingredient | 10.0 mg |
| 2. Polyethylene Glycol 1000 | 1350.0 mg |
| 3. Polyethylene Glycol 4000 | 450.0 mg |

Procedure
1. Melt 2 and 3 together and stir until uniform.
2. Dissolve #1 in the molten mass from step #1 and stir until uniform.
3. Pour the molten mass from step #2 into suppository molds and chill.
4. Remove the suppositories from molds and wrap.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:
1. A compound having the formula:

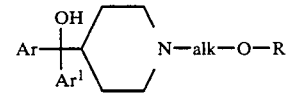

wherein Ar and $Ar^1$ can be independently phenyl, 2, 3 or 4-pyridinyl, or

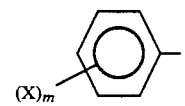

where X is selected from halogen, trifluoromethyl, loweralkyl, loweralkoxy, or hydroxy and m is 0–3, "alk" is a straight or branched hydrocarbon chain containing 2-12 carbons;

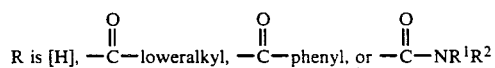

where $R^1$ and $R^2$ are independently selected from H, loweralkyl, phenyl, or

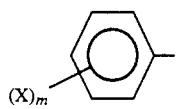

as defined above; the optical isomers and the pharmaceutically acceptable acid addition salts thereof.

2. Compounds of claim 1 which are:
4-[bis(4-fluorophenyl)hydroxymethyl]-1-piperidinepropanol acetic ester,
4-[bis(4-fluorophenyl)hydroxymethyl]-1-piperidinepropanol benzoate ester,
3-[4-[Bis(4-fluorophenyl)hydroxymethyl]-1-piperidinyl]-propanol dimethylcarbamate ester,
4-[bis(4-fluorophenyl)hydroxymethyl]-1-piperidinepropanol methyl carbamate ester,
4-[bis(4-fluorophenyl)hydroxymethyl]-1-piperidinepropanol phenylcarbamate ester,
3-[4-[Bis(4-fluorophenyl)hydroxymethyl]-1-piperidinyl]propanol diphenyl carbamate ester,
3-[4-[Bis(4-fluorophenyl)hydroxymethyl]-1-piperidinyl]propanol methyl phenyl carbamate ester,
4-[bis(4-fluorophenyl)hydroxymethyl]-1-piperidineethanol methylcarbamate ester,
4-[bis(4-fluorophenyl)hydroxymethyl]-1-piperidinebutanol methylcarbamate ester,
4-[bis(4-fluorophenyl)hydroxymethyl]-1-piperidineoctanol methylcarbamate ester,
4-[bis(4-fluorophenyl)hydroxymethyl]-1-piperidinehexanol methylcarbamate ester,
4-[bis(4-fluorophenyl)hydroxymethyl]-1-piperidineethanol dimethylcarbamate ester,
4-[bis(4-fluorophenyl)hydroxymethyl]-1-piperidinepentanol methylcarbamate ester,
4-[bis(4-fluorophenyl)hydroxymethyl]-1-piperidinebutanol dimethylcarbamate ester and the optical isomers and pharmaceutically acceptable acid addition salts thereof.

3. A method of treating allergic disorders in warm blooded animals which comprises administering to said animals a therapeutically effective amount for treating allergic disorders of a compound having the formula:

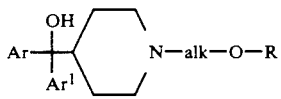

wherein Ar and $Ar^1$ can be independently phenyl, 2, 3 or 4-pyridinyl, or

where X is selected from halogen, trifluoromethyl, loweralkyl, loweralkoxy, or hydroxy and m is 0–3, "alk" is a straight or branched hydrocarbon chain containing 2-12 carbons;

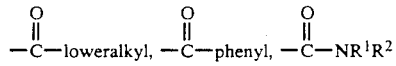

where $R^1$ and $R^2$ are independently selected from H, loweralkyl, phenyl, or

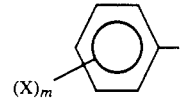

as defined above; the optical isomers and the pharmaceutically acceptable acid addition salts thereof.

4. The method of claim 3 wherein the compound used for treating allergic disorders is selected from:
4-[bis(4-fluorophenyl)hydroxymethyl]-1-piperidinepropanol acetic ester,
4-[bis(4-fluorophenyl)hydroxymethyl]-1-piperidinepropanol benzoate ester,
3-[4-[Bis(4-fluorophenyl)hydroxymethyl]-1-piperidinyl]-propanol dimethylcarbamate ester,
4-[bis(4-fluorophenyl)hydroxymethyl]-1-piperidinepropanol methyl carbamate ester,
4-[bis(4-fluorophenyl)hydroxymethyl]-1-piperidinepropanol phenylcarbamate ester,
3-[4-[Bis(4-fluorophenyl)hydroxymethyl]-1-piperidinyl]propanol diphenyl carbamate ester,
3-[4-[Bis(4-fluorophenyl)hydroxymethyl]-1-piperidinyl]propanol methyl phenyl carbamate ester,
4-[bis(4-fluorophenyl)hydroxymethyl]-1-piperidineethanol methylcarbamate ester,
4-[bis(4-fluorophenyl)hydroxymethyl]-1-piperidinebutanol methylcarbamate ester,
4-[bis(4-fluorophenyl)hydroxymethyl]-1-piperidineoctanol methylcarbamate ester,
4-[bis(4-fluorophenyl)hydroxymethyl]-1-piperidinehexanol methylcarbamate ester,
4-[bis(4-fluorophenyl)hydroxymethyl]-1-piperidineethanol dimethylcarbamate ester,
4-[bis(4-fluorophenyl)hydroxymethyl]-1-piperidinepentanol methylcarbamate ester,
4-[bis(4-fluorophenyl)hydroxymethyl]-1-piperidinebutanol dimethylcarbamate ester and the optical isomers and pharmaceutically acceptable acid addition salts thereof.

5. A pharmaceutical composition suitable for the treatment of allergic disorders in a living animal comprising a. A therapeutically effective amount for the treatment of allergic disorders of a compound selected from the group having the formula:

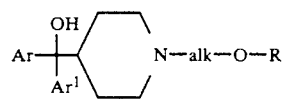

wherein Ar and $Ar^1$ can be independently phenyl, 2, 3 or 4-pyridinyl, or

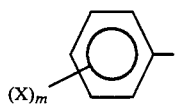

where X is selected from halogen, trifluoromethyl, loweralkyl, loweralkoxy, or hydroxy and m is 0-3, "alk" is a straight or branched hydrocarbon chain containing 2-12 carbons;

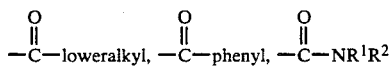

where $R^1$ and $R^2$ are independently selected from H, loweralkyl, phenyl, or

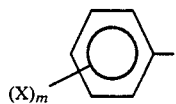

as defined above; the optical isomers and the pharmaceutically acceptable acid addition salts thereof, and b. a pharmaceutically acceptable carrier.

6. A pharmaceutical composition according to claim 5 wherein the compound used is selected from:

4-[bis(4-fluorophenyl)hydroxymethyl]-1-piperidinepropanol acetic ester,
4-[bis(4-fluorophenyl)hydroxymethyl]-1-piperidinepropanol benzoate ester,
3-[4-[Bis(4-fluorophenyl)hydroxymethyl]-1-piperidinyl]-propanol dimethylcarbamate ester,
4-[bis(4-fluorophenyl)hydroxymethyl]-1-piperidinepropanol methyl carbamate ester,
4-[bis(4-fluorophenyl)hydroxymethyl]-1-piperidinepropanol phenylcarbamate ester,
3-[4-[Bis(4-fluorophenyl)hydroxymethyl]-1-piperidinyl]propanol diphenyl carbamate ester,
3-[4-[Bis(4-fluorophenyl)hydroxymethyl]-1-piperidinyl]propanol methyl phenyl carbamate ester,
4-[bis(4-fluorophenyl)hydroxymethyl]-1-piperidineethanol methylcarbamate ester,
4-[bis(4-fluorophenyl)hydroxymethyl]-1-piperidinebutanol methylcarbamate ester,
4-[bis(4-fluorophenyl)hydroxymethyl]-1-piperidineoctanol methylcarbamate ester,
4-[bis(4-fluorophenyl)hydroxymethyl]-1-piperidinehexanol methylcarbamate ester,
4-[bis(4-fluorophenyl)hydroxymethyl]-1-piperidineethanol dimethylcarbamate ester,
4-[bis(4-fluorophenyl)hydroxymethyl]-1-piperidinepentanol methylcarbamate ester,
4-[bis(4-fluorophenyl)hydroxymethyl]-1-piperidinebutanol dimethylcarbamate ester and the optical isomers and pharmaceutically acceptable acid addition salts thereof.

* * * * *